United States Patent [19]

Itoh et al.

[11] Patent Number: 4,876,344

[45] Date of Patent: Oct. 24, 1989

[54] NOVEL ORGANOSILICON COMPOUNDS

[75] Inventors: Kunio Itoh; Motoo Fukushima; Tsutomu Nakamura, all of Annaka, Japan

[73] Assignee: Shin-Etsu Chemical Co., Ltd., Tokyo, Japan

[21] Appl. No.: 277,632

[22] Filed: Nov. 29, 1988

[30] Foreign Application Priority Data

Dec. 9, 1987 [JP] Japan ............................. 62-311764

[51] Int. Cl.$^4$ ........................................... C07D 251/38
[52] U.S. Cl. ................................................. 544/219
[58] Field of Search ...................................... 544/219

[56] References Cited

U.S. PATENT DOCUMENTS 3,366,598  1/1968  Westlinning et al. ............... 544/219

*Primary Examiner*—Mary C. Lee
*Assistant Examiner*—J. Richter
*Attorney, Agent, or Firm*—Lowe, Price, LeBlanc, Becker & Shur

[57] ABSTRACT

Organosilicon compounds of the following formula, or hydrolyzates thereof, t,0010 ps in which Rhu 1 1 and Rhu 2 1 are independently a hydrogen atom or an alkyl group having from 1 to 8 carbon atoms, m is an integer of from 1 to 8, and n is an integer of from 1 to 3. The compound is useful as a vulcanizing agent particularly for vulcanizable elastomer compositions comprising inorganic fillers.

7 Claims, 2 Drawing Sheets

NOVEL ORGANOSILICON COMPOUNDS

BACKGROUND OF THE INVENTION

1. Field of the Invention

This invention relates to hitherto unknown, novel organosilicon compounds which are particularly useful as a crosslinking agent for vulcanizable compositions of elastomers having active halogen atoms or epoxy groups. When vulcanized, the composition exhibits high mechanical strength, high crosslinking density and high heat resistance.

2. Description of the Prior Art

A variety of silane coupling agents are known including compounds which have, respectively, combinations of at least one hydrolyzable alkoxy group and other functional groups. For instance, a typical silane coupling agent is a compound of the following formula having methoxy groups and a mercapto group, $HSC_3H_6Si(OCH_3)_3$.

In United States Patent No. 3,366,598, there are described curing or vulcanizing agents having a trithiocyanuric acid group of the following formula

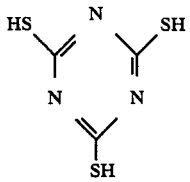

with or without modification of one mercapto group with an amino group as shown in the following formula

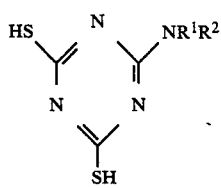

in which $R^1$ and $R^2$ independently represent a hydrogen atom or an alkyl group.

These curing agents are able to react with an unvulcanized elastomer composition to cure the composition. However, if the composition contains inorganic compounds, such as silica, as a filler, the curing agents which do not react with the inorganic compound tend to bloom or dissipate by sublimation during storage prior to vulcanization.

SUMMARY OF THE INVENTION

It is accordingly an object of the invention to provide a silane coupling agent which is a hitherto unknown, novel organosilicon compound and is able to cure vulcanizable elastomer compositions comprising inorganic fillers.

It is another object of the invention to provide a silane coupling agent which has groups capable of reaction with inorganic fillers such as silica whereby when the agent is added to unvulcanized elastomer compositions containing such inorganic fillers, it does not dissipate or bloom.

It is a further object of the invention to provide a silane coupling agent which is useful as a curing and crosslinking agent when added to unvulcanized elastomer compositions whereby the resultant vulcanized product has good physical properties.

The present invention contemplates to provide a novel organosilicon compound of the following general formula (1)

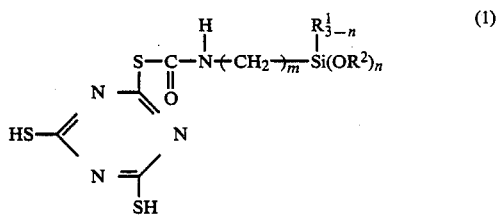

in which $R^1$ and $R^2$ independently represents a hydrogen atom and an alkyl group having from 1 to 8 carbon atoms, m is an integer of from 1 to 8, and n is an integer of from 1 to 3.

DETAILED DESCRIPTION AND EMBODIMENTS OF THE INVENTION

Figure 1:
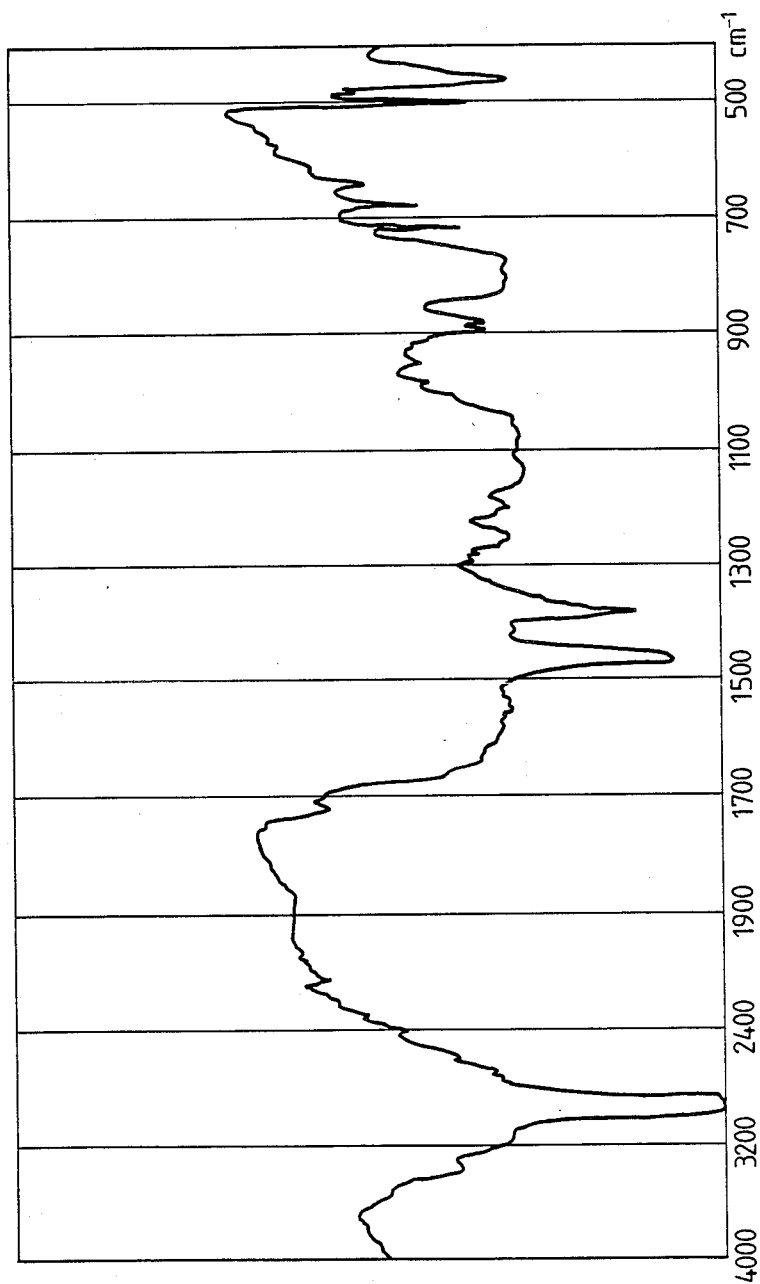
FIG. 1 is an IR absorption spectrum of the compound obtained in Example 1.

The hitherto unknown, novel silane compound of the invention are of the following formula (1)

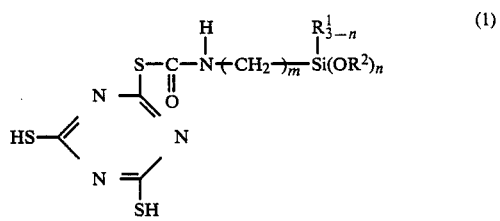

in which $R^1$, $R^2$, m and n have, respectively, the same meanings as defined above. The alkyl group represented by $R^1$ and $R^2$ should have from 1 to 8 carbon atoms. Specific examples of the alkyl group include a methyl group, an ethyl group, a propyl group, a butyl group, a pentyl group, a hexyl group, a heptyl group and an octyl group. In the formula (1), it is preferred that $R^1$ and $R^2$ independently represent an alkyl group having from 1 to 3 carbon atoms, m=3 and n=3. This is for the following reasons. The compound of the formula (1) wherein $R^1$ and $R^2$ independently represent 1 to 3 carbon atoms are advantageous in ease for hydrolysis. The compound of the formula (1) wherein n=3 is easier in preparation than compounds having a smaller value of n. Moreover, the compound (1) wherein n=3 has so many a hydrolyzable groups that coupling to an inorganic filler such as silica becomes strong in a final product. Specific and preferable examples of the silane compound according to the invention are those of the following formulae (2) to (4)

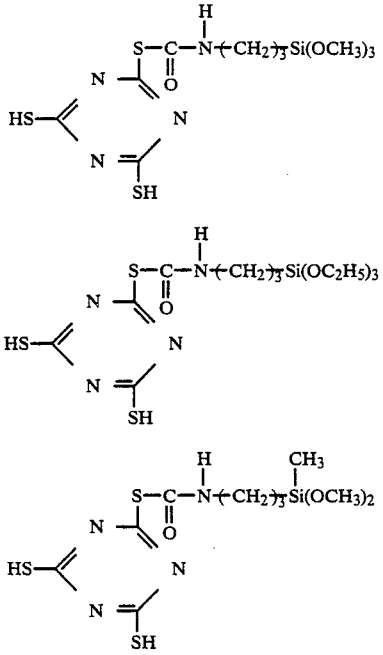

The silane compounds of the invention are prepared in the following manner. Trithiocyanuric acid is first dissolved in an organic solvent such as tetrahydrofuran. An alkoxysilane of the following formula (5) having an isocyanate group is added to the solution for reaction

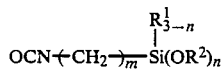
(5)

The reaction is effected at a temperature of from 0 to 80° C., preferably from 50 to 70° C., for a time of from 0.5 to 5 hours. After completion of the reaction, the solvent is stripped off under reduced pressure to obtain a product. In order to effectively cause the reaction to proceed, it is preferred to effect the reaction in the presence of a catalyst such as a Lewis acid such as a titanium compound, a tin compound or the like. In this case, the reaction may proceed at room temperature.

The organosilicon compounds of the formula (1) are novel compounds and have wide utility. Especially, they are useful as a vulcanizing agent for compositions of vulcanizable elastomers containing active halogens or epoxy groups, e.g. acrylic elastomers. The compounds exhibit low volatility and chemically combine with inorganic compounds, such as silica, alumina or clay, because the alkoxy moieties readily undergo hydrolysis. Accordingly, the compounds are especially effective for use as a curing and crosslinking agent for vulcanizable elastomer compositions comprising the inorganic fillers or compounds as will not be realized in prior art agents. The resulting cured elastomer composition has high mechanical strength including a high tensile strength, a high crosslinking density and a high heat resistance. It should be noted that although the organosilicon compounds of the invention may be used, as it is, as a coupling agent, the alkoxy moieties may be hydrolyzed into hydroxyl groups prior to the application, if necessary. Accordingly, the organosilicon compounds whose alkoxy groups are completely hydrolyzed or further partially condensed may also be used as a coupling agent in the practice of the invention. The hydrolysis may be effected, for example, by adding a mineral acid or Lewis acid to an aqueous solution of the organosilicon compound. The resultant hydrolyzate may be readily partially condensed.

In practice, when the organosilicon compounds of the invention are thermally treated at about 80° to 140° C. in coexistence with an inorganic filler such as silica, they readily react with the silica by partial hydrolysis and/or condensation of the compounds. The hydrolysis or condensation may be facilitated by adding a dilute acid such as about 1% hydrochloric acid is added along with the inorganic filler. In this condition, the resultant hydrolyzate spontaneously condenses with silica or the like.

The present invention is more particularly described by way of examples and applications of organosilicon compounds of the invention, in which parts are by weight.

EXAMPLE 1

17.7 g (0.1 mole) of tricyanuric acid was dissolved in 100 ml of tetrahydrofuran, to which 20.5 g (0.1 mole) of trimethoxysilane of the following formula having an isocyanate group, O C N(CH₂)₃S i (O C H₃)₃ and 0.08 g (0.2 wt%) of dibutyldistearyl tin used as a catalyst were added, whereupon heat generated and the reaction proceeded. The reaction system was agitated at 60° C. for 1 hour to complete the reaction. The tetrahydrofuran was stripped off under reduced pressure to obtain 3 g (yield 98%) of a white solid.

The thus obtained solid product was subjected to IR absorption spectrum analysis and NMR analysis. The IR absorption spectrum is shown in FIG. 1. The results of the NMR analysis are as follows.

NMR (CDCl₃):

δ 0.11–0.85(m)    Si—CH₂    (2H)

δ 1.6–1.8(m)    CH₂CH₂—CH₂    (2H)

δ 2.85–3.02(m)    CH₂—CH₂—CH₂—N(H)    (2H)

δ 3.47(S)    Si(OCH₃)₃    (9H)

From the above results, it was confirmed that the product was a compound of the following formula

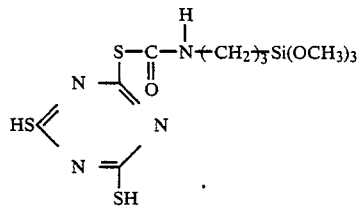

This compound is hereinafter referred to simply as A-1.

Figure 2:
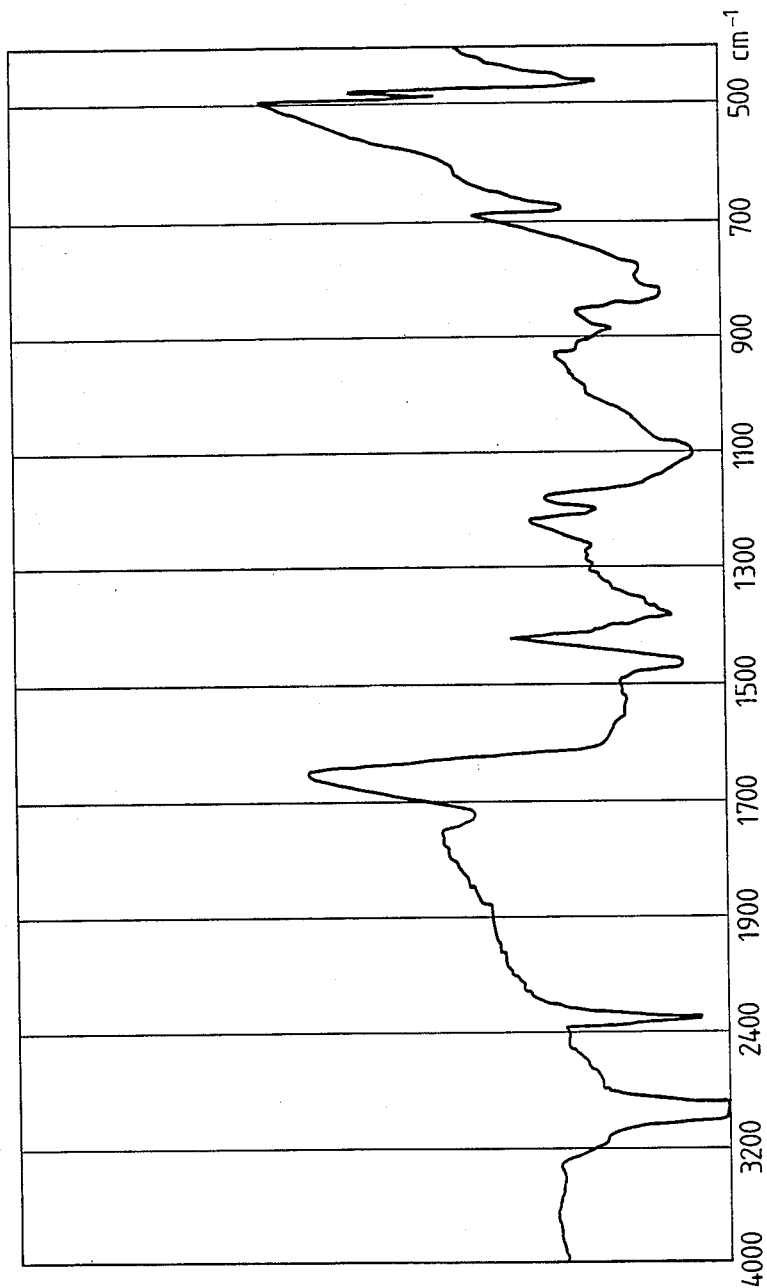
FIG. 2 is an IR absorption spectrum of the reaction product obtained in Example 1 without addition of a tin catalyst.

From the above results, it was confirmed that the product was a compound of the following formula The above procedure was repeated without use of any tin catalyst. As a result, it was found that the reaction did not complete. The IR absorption of the resultant product is shown in FIG. 2, revealing the existence of the isocyanate group.

EXAMPLE 2

The general procedure of Example 1 was repeated except that the trimethoxysilane was replaced by 24.7 g (0.1 mole) of triethoxysilane of the following formula having an isocyanate group, thereby obtaining 41 g of a white solid The solid product was subjected to NMR analysis. The results are shown below.

NMR (CDCl$_3$, TMS):

δ 0.10–0.84(mm)   Si—CH$_2$   (2H)

δ 1.6–1.8(m)   CH$_2$CH$_2$—CH$_2$   (2H)

δ 1.75(t)   Si(OCH$_2$—CH$_3$)$_3$   (9H)

δ 2.85–3.02(m)   CH$_2$—CH$_2$—CH$_2$—N(H)   (2H)

δ 3.51(g)   Si(OCH$_2$—CH$_3$)$_3$   (6H)

From the above results, it was confirmed that the product was a compound of the following formula

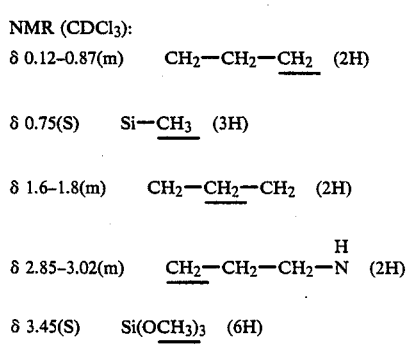

This compound is hereinafter referred to simply as A-2.

EXAMPLE 3

The general procedure of Example 1 was repeated except that the trimethoxysilane was replaced by methyldimethoxysilane of the following formula having an isocyanate group, thereby obtaining 41 g of a white solid The solid product was subjected to NMR analysis. The results are shown below.

NMR (CDCl$_3$):

δ 0.12–0.87(m)   CH$_2$—CH$_2$—CH$_2$   (2H)

δ 0.75(S)   Si—CH$_3$   (3H)

δ 1.6–1.8(m)   CH$_2$—CH$_2$—CH$_2$   (2H)

δ 2.85–3.02(m)   CH$_2$—CH$_2$—CH$_2$—N(H)   (2H)

δ 3.45(S)   Si(OCH$_3$)$_3$   (6H)

From the above results, it was confirmed that the product was a compound of the following formula

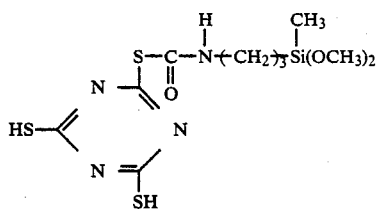

This compound is hereinafter referred to simply as A-3. Examples 4–6 and Comparative Examples 1, 2.

78 parts of ethyl acrylate, 20 parts of butyl acrylate and 2 parts of vinyl chloroacetate were copolymerized to obtain a polyacrylate. To the polyacrylate were added 50 parts of a silica powder (Aerosil 200, available from Nippon Aerosil, o., Ltd.) or 50 parts of silica powder (Nipsil LP, available from Nippon Silica Ind. Co., Ltd.), 1 part of stearic acid, 5 parts or 3 parts of alpha, omegadihydroxydimethylpolysiloxane, 2 parts of Naugard 445 (a substituted diphenylamine antioxidant, available from Uniroyal Chemical Co., Ltd.), 4 parts of magnesium oxide, and 1.2 parts of Nocceler pz (zinc dimethyl dithiocarbonate, available from Ohuchi Sinkou Chem. Ind. Co., Ltd.). The mixture was uniformly mixed to obtain an elastomer composition. The silane compounds A-1 to A-3 obtained in Examples 1 to 3 were added to the elastomer composition and kneaded.

Each composition was subjected to hot pressing for vulcanization under conditions of 165° C., 40 kg/cm$^2$ and 2 minute to obtain a 2 mm thick rubber sheet, followed by after-vulcanization at 180° C. for 8 hours. The physical properties of the responsive sheet were determined with the results shown in the table. From the results, it will be seen that these sheets have a high 100 modulus and a high tear strength.

Moreover, the respective sheets were each heated at 180° C. for 24 hours or immersed in an oil at 150° C. for 7 hours, followed by measurement of physical properties. The results are also shown in the table, revealing that the cured sheets have good resistances to heat and oil.

For comparison, the above procedure was repeated except that the compounds A-1 to A-3 were replaced by a compound of the following formula (Zisnet F, available from Sankyo Chem. Co., Ltd.)

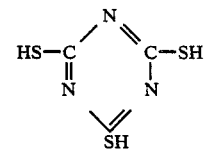

and the above-indicated compound in which one SH group is substituted with a —N(C$_4$H$_9$)$_2$ group (Zisnet DB), thereby obtaining cured products. Similarly, the products were subjected to measurement of physical properties. The results are also shown in the table. It will be seen that these comparative products are inferior in 100% modulus, tear strength and heat and oil resistances to those of the invention.

TABLE

| | Example No. | | | Comparative Example No. | |
|---|---|---|---|---|---|
| | 4 | 5 | 6 | 1 | 2 |
| Elastomer Composition (parts): | | | | | |
| raw rubber | 100 | 100 | 100 | 100 | 100 |
| silica (Aerosil 200) | 50 | 50 | — | 50 | 50 |
| silica (Nipsil LD) | — | — | 50 | — | — |
| stearic acid | 1 | 1 | 1 | 1 | 1 |
| alpha, omega-dihydroxy-dimethylpolysiloxane | 5 | 5 | 3 | 5 | 5 |
| Naugard 445 | 2 | 2 | 2 | 2 | 2 |
| MgO | 4 | 4 | 4 | 4 | 4 |
| PZ | 1.2 | — | 1.2 | 1.2 | 1.2 |
| vulcanizing agent | A-1 | A-2 | A-3 | Zisnet F | Zisnet DB |
| | 1.2 | 1.2 | 1.2 | 1.2 | 1.2 |
| Physical Properties After Curing: | | | | | |
| hardness (JIS) | 75 | 73 | 68 | 72 | 68 |
| elongation (%) | 300 | 310 | 255 | 330 | 380 |
| tensile strength (kg/cm$^2$) | 126 | 125 | 108 | 110 | 140 |
| tear strength (kg/cm) | 38 | 36 | 31 | 27 | 28 |
| 100% modulus (kg/cm$^2$) | 33 | 32 | 28 | 24 | 19 |
| Compression Set (150° C. × 22 hrs)(%) | 30 | 33 | 25 | 44 | 40 |
| Heat Resistance: | | | | | |
| variation in hardness after treatment at 180° C. × 24 hrs. | +3 | +4 | +4 | +5 | +8 |
| variation in tensile st. | −2 | −8 | −5 | −13 | −15 |
| variation in elongation | −10 | −18 | −8 | −11 | −12 |
| Oil Resistance: | | | | | |
| variation in hardness after treatment in JIS #3 oil of 150° C. for 7 hrs. | −10 | −7 | −8 | −11 | −9 |
| variation in tensile st. | −25 | −18 | −23 | −24 | −28 |
| variation in elongation | −17 | −18 | −11 | −40 | −24 |
| variation in volume | +19 | +18 | +18 | +28 | +21 |
| Scorching (1) | no | no | no | no | yes |
| Blooming (2) | no | no | no | yes | yes |

(1) Each composition comprising vulcanizing agent was kneaded at room temperature, allowed to stand for one day, and again kneaded where upon "Scorching" was determined as "no" when the re-kneading was possible and as "yes" when the re-kneading was not possible.
(2) "Blooming" was determined as "no" when white powder was not found through visual observation on a vulcanized rubber sheet after allowing it to stand for three days at room temperature and as "yes" when white powder was found.

What is claimed is:

1. An organosilicon compound of the following formula, or a hydrolyzate thereof

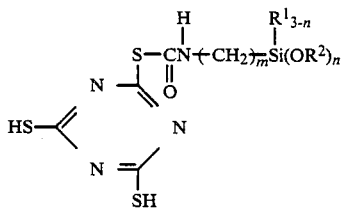

wherein R$^1$ and R$^2$ independently represent a hydrogen atom or an alkyl group having from 1 to 8 carbon atoms, m is an integer of from 1 to 6 and n is an integer of from 1 to 3.

2. An organisilicon compound according to claim 1, wherein R$^1$ and R$^2$ independently represent an alkyl group having from 1 to 3 carbon atoms, m=3 and n=3.

3. An organosilicon compound according to claim 1, wherein said organosilicon compound is in the form of a hydrolyzate.

4. An organosilicon compound according to claim 3, wherein the hydrolyzate is partially condensed.

5. An organosilicon compound of the following formula, or a hydrolyzate thereof,

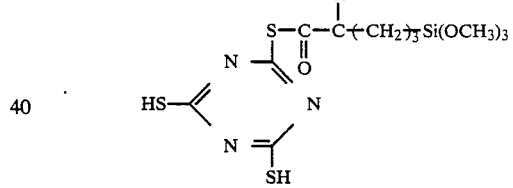

6. An organosilicon compound of the following formula, or a hydrolyzate thereof,

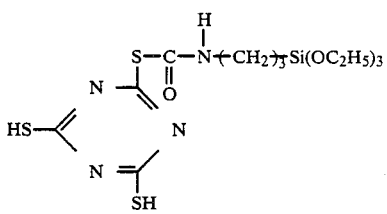

7. An organosilicon compound of the following formula, or a hydrolyzate thereof,

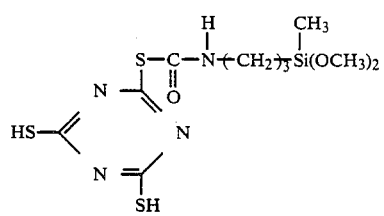

* * * * *